(12) United States Patent
Alfery

(10) Patent No.: US 6,983,744 B2
(45) Date of Patent: *Jan. 10, 2006

(54) PERILARYNGEAL ORAL AIRWAY WITH TEMPERATURE SENSOR

(76) Inventor: David D. Alfery, 22 Wynstone, Nashville, TN (US) 37215

( * ) Notice: Subject to any disclaimer, the term of this patent is extended or adjusted under 35 U.S.C. 154(b) by 0 days.

This patent is subject to a terminal disclaimer.

(21) Appl. No.: 10/818,681

(22) Filed: Apr. 5, 2004

(65) Prior Publication Data

US 2004/0182384 A1 Sep. 23, 2004

Related U.S. Application Data

(63) Continuation of application No. 10/145,389, filed on May 14, 2002, now Pat. No. 6,729,325, which is a continuation of application No. 09/409,295, filed on Sep. 29, 1999, now Pat. No. 6,386,199.

(51) Int. Cl.
*A61M 16/00* (2006.01)

(52) U.S. Cl. .......................... 128/200.26; 128/207.14; 128/207.15; 600/549

(58) Field of Classification Search .......... 128/207.14, 128/207.15, 200.26; 600/474, 549
See application file for complete search history.

(56) References Cited

U.S. PATENT DOCUMENTS

| | | |
|---|---|---|
| 2,220,493 A | 11/1940 | Pixler |
| 3,421,510 A | 1/1969 | Kettenbach |
| 3,756,244 A | 9/1973 | Kinnear et al. |
| 3,774,616 A | 11/1973 | White |
| 3,908,665 A | 9/1975 | Moses |
| 4,046,139 A | 9/1977 | Horn |
| 4,054,135 A | 10/1977 | Berman |
| 4,063,561 A | 12/1977 | McKenna |
| 4,067,331 A | 1/1978 | Berman |
| 4,158,916 A | 6/1979 | Adler |
| 4,263,921 A | 4/1981 | Trugillo |
| 4,265,621 A | 5/1981 | McVey |
| D261,442 S | 10/1981 | Anderson |
| 4,321,921 A | 3/1982 | Laszczower |
| 4,338,930 A | 7/1982 | Williams |
| 4,383,534 A | 5/1983 | Peters |
| 4,454,887 A | 6/1984 | Kruger |
| 4,497,324 A | 2/1985 | Sullivan et al. |
| 4,502,482 A | 3/1985 | DeLuccia et al. |
| 4,509,514 A | 4/1985 | Brain |
| 4,527,553 A | 7/1985 | Upsher |
| 4,612,927 A | 9/1986 | Kruger |
| 4,683,879 A | 8/1987 | Williams |
| 4,685,447 A | 8/1987 | Iversen et al. |
| 4,759,356 A | 7/1988 | Muir |
| 4,796,640 A | 1/1989 | Webler |

(Continued)

FOREIGN PATENT DOCUMENTS

GB 1535060 12/1978

(Continued)

*Primary Examiner*—Mital Patel
(74) *Attorney, Agent, or Firm*—Swanson & Bratschun LLC

(57) ABSTRACT

An oral airway (510) includes an elongate tubular member (512) having a distal (510) and a proximal end (514), the oral airway being configured to place the distal end in a supraglottic position and prevent insertion of the distal end into the patient's larynx when operatively placed within the hypopharynx of a patient. A temperature sensor (554) is operatively associated with the elongate tubular member to detect a core temperature of a patient with the distal end of the oral airway operatively placed in a supraglottic position within the hypopharynx of the patient.

16 Claims, 16 Drawing Sheets

U.S. PATENT DOCUMENTS

| | | |
|---|---|---|
| 4,825,858 A | 5/1989 | Frankel |
| 4,827,910 A | 5/1989 | Mathews, II |
| 4,832,020 A | 5/1989 | Augustine |
| 4,848,331 A | 7/1989 | Northway-Meyer |
| 4,852,565 A | 8/1989 | Eisele |
| 4,919,126 A | 4/1990 | Baildon |
| 4,976,261 A | 12/1990 | Gluck et al. |
| 5,038,766 A | 8/1991 | Parker |
| 5,057,106 A | 10/1991 | Kasevich et al. |
| 5,163,423 A | 11/1992 | Suzuki |
| 5,174,283 A | 12/1992 | Parker |
| 5,176,692 A | 1/1993 | Wilk et al. |
| 5,203,320 A | 4/1993 | Augustine |
| 5,295,489 A | 3/1994 | Bell et al. |
| 5,303,697 A | 4/1994 | Brain |
| 5,323,771 A | 6/1994 | Fisher et al. |
| 5,339,805 A | 8/1994 | Parker |
| 5,356,391 A | 10/1994 | Stewart |
| 5,357,954 A | 10/1994 | Shigezawa et al. |
| 5,365,940 A | 11/1994 | Teves |
| 5,443,063 A | 8/1995 | Greenberg |
| 5,477,851 A | 12/1995 | Callaghan et al. |
| 5,499,970 A | 3/1996 | Olson |
| 5,562,608 A | 10/1996 | Sekins et al. |
| 5,622,182 A | 4/1997 | Jaffe |
| 5,653,229 A | 8/1997 | Greenberg |
| 5,720,275 A | 2/1998 | Patil et al. |
| 5,743,254 A | 4/1998 | Parker |
| 5,743,258 A | 4/1998 | Sato et al. |
| 5,746,202 A | 5/1998 | Pagan |
| 5,771,889 A | 6/1998 | Pagan |
| 5,819,733 A | 10/1998 | Bertram |
| 5,853,004 A | 12/1998 | Goodman |
| 5,873,362 A | 2/1999 | Parker |
| 5,878,745 A | 3/1999 | Brain |
| 5,896,858 A | 4/1999 | Brain |
| 5,906,584 A | 5/1999 | Pavoni et al. |
| 6,001,077 A | 12/1999 | Ellman et al. |
| 6,168,579 B1 | 1/2001 | Tsugita |
| 6,256,524 B1 | 7/2001 | Walker et al. |
| 6,386,199 B1 | 5/2002 | Alfery |
| 6,729,325 B2 * | 5/2004 | Alfery .................. 128/200.26 |

FOREIGN PATENT DOCUMENTS

WO     WO 92/13587     8/1992

* cited by examiner

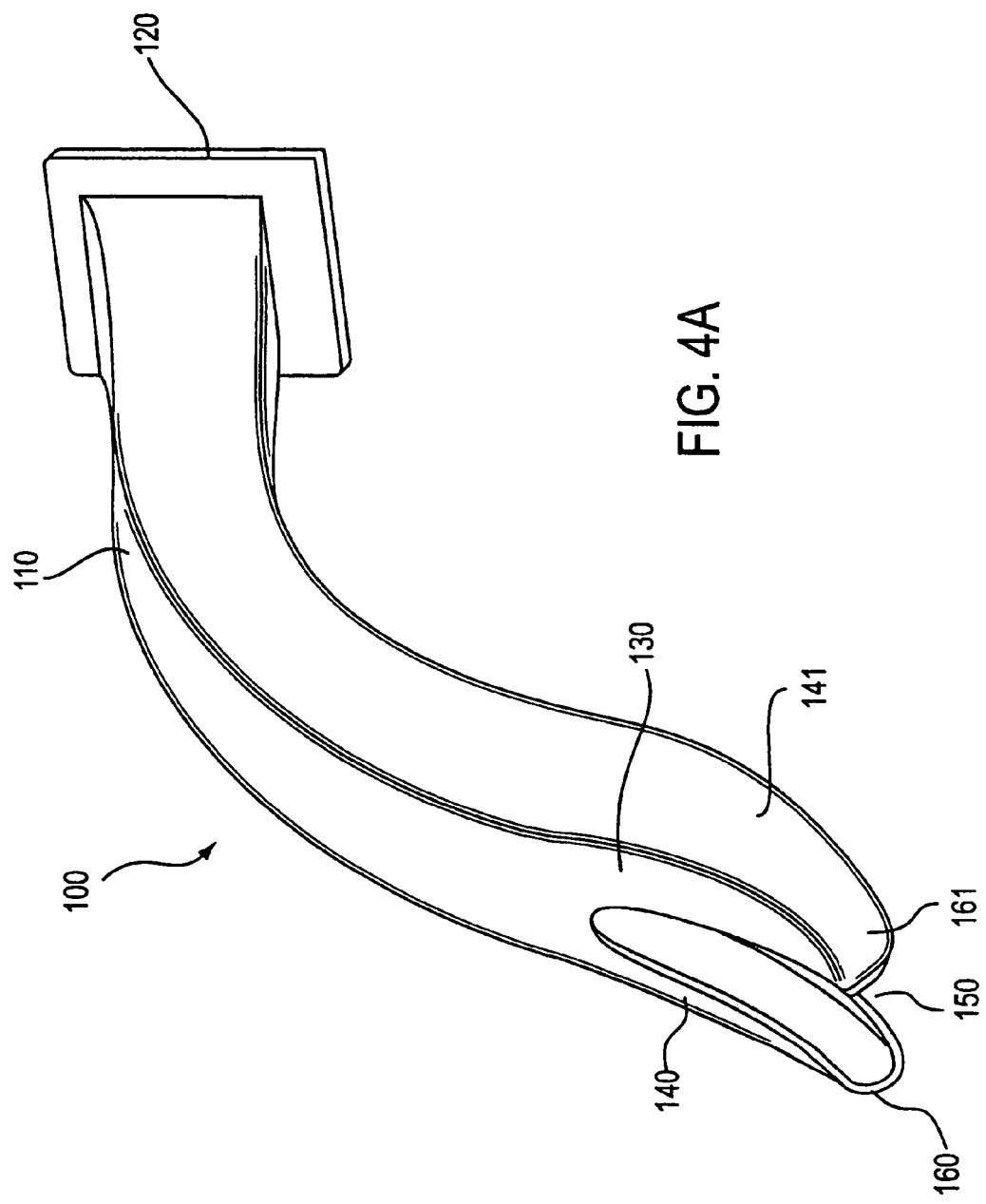

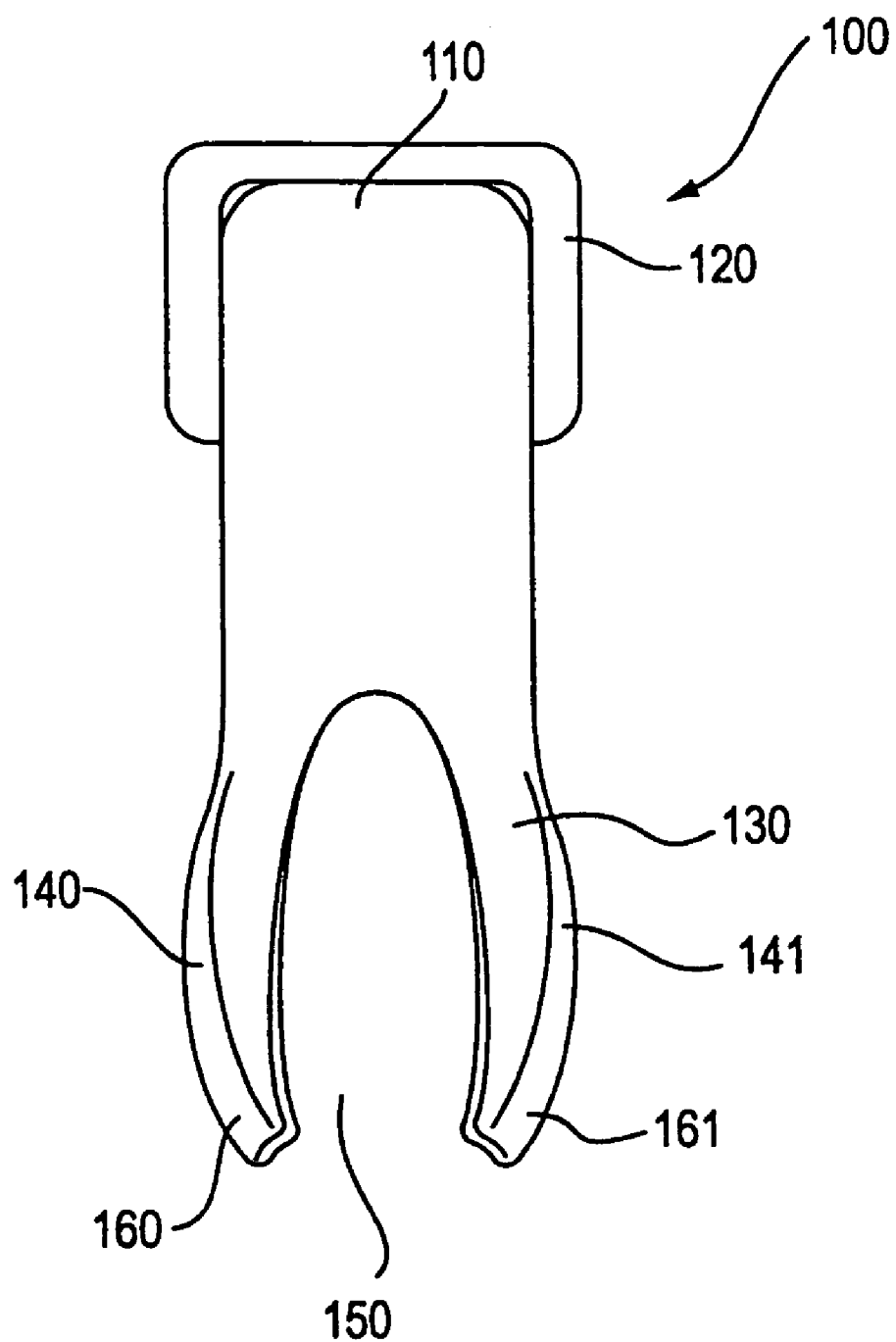

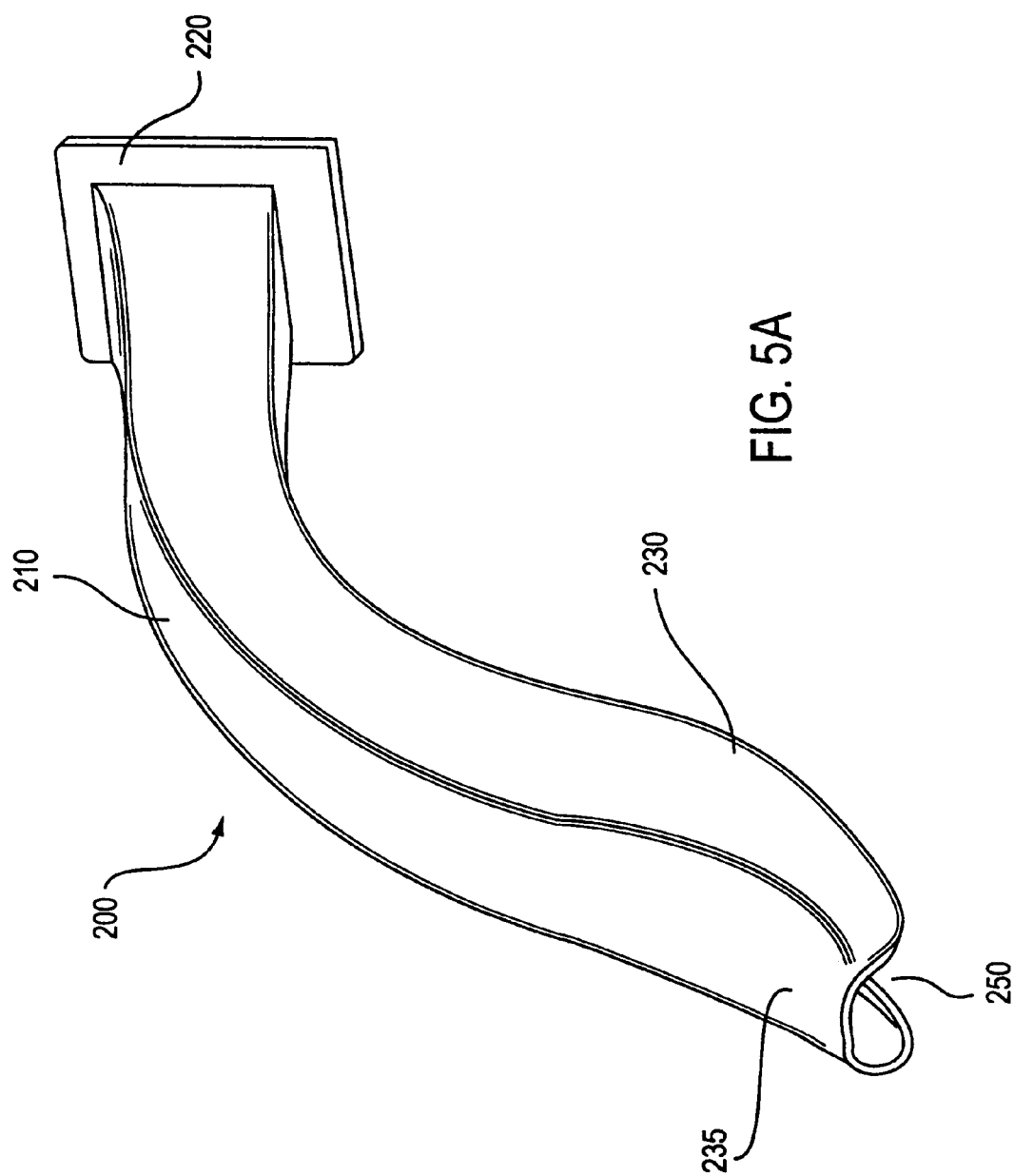

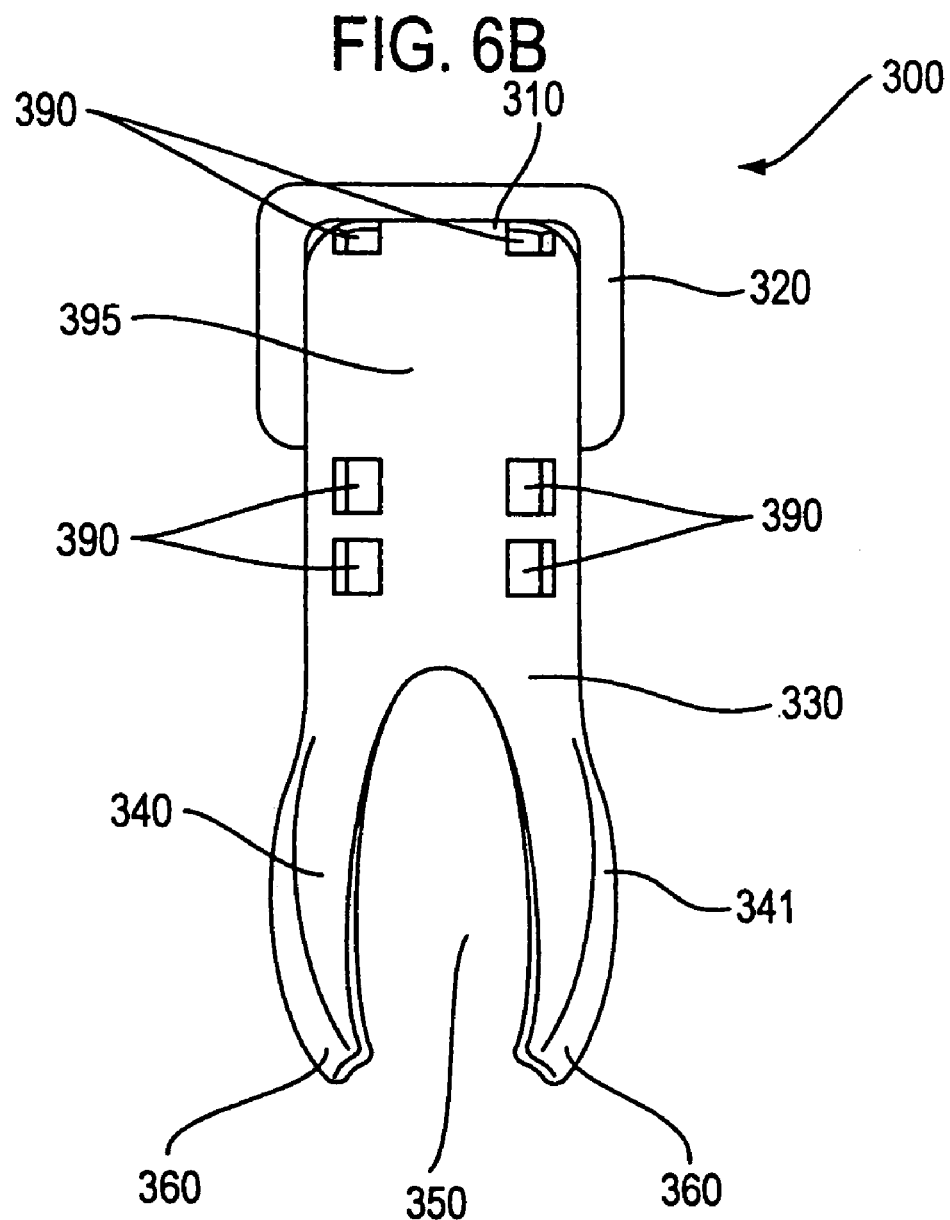

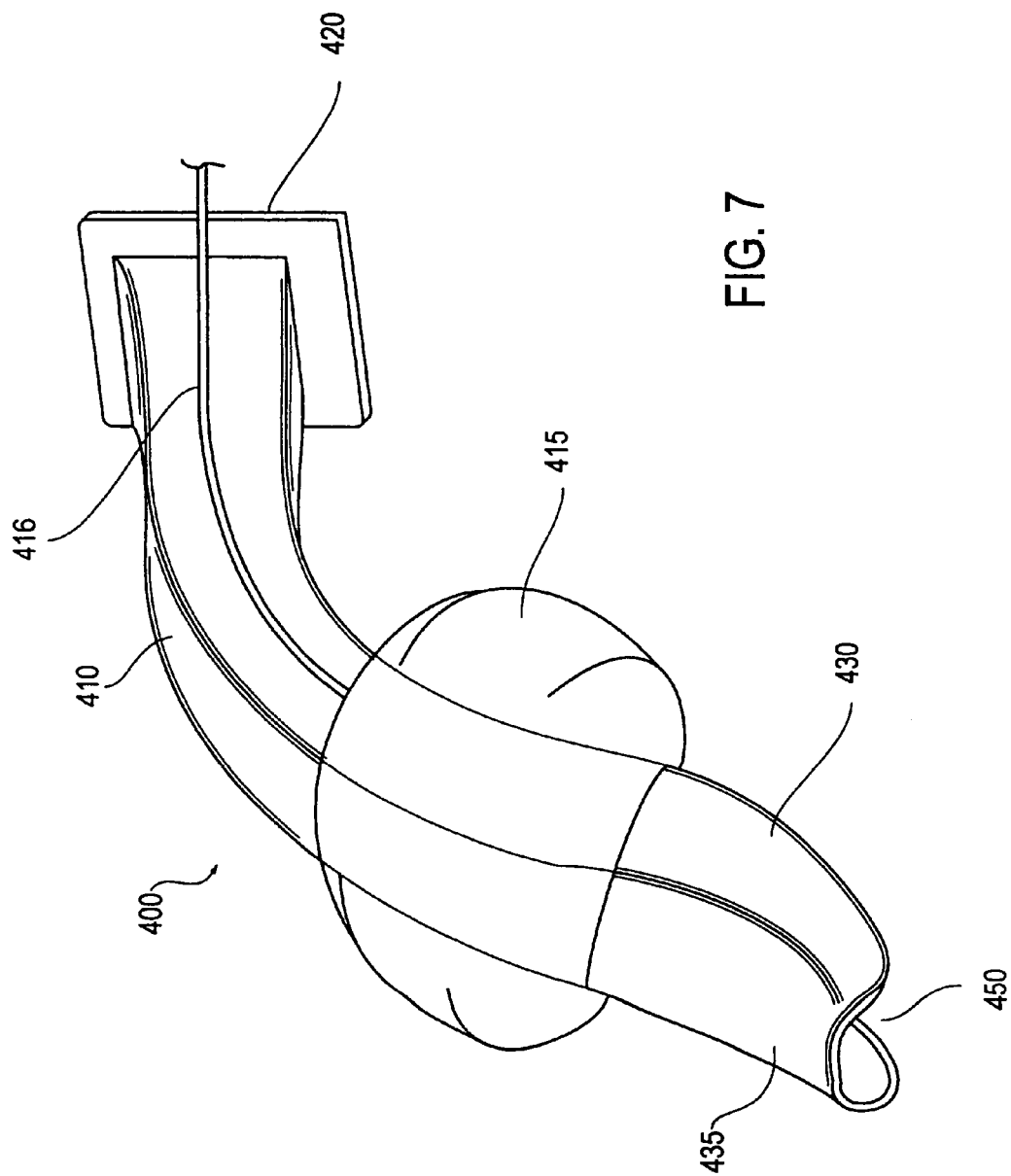

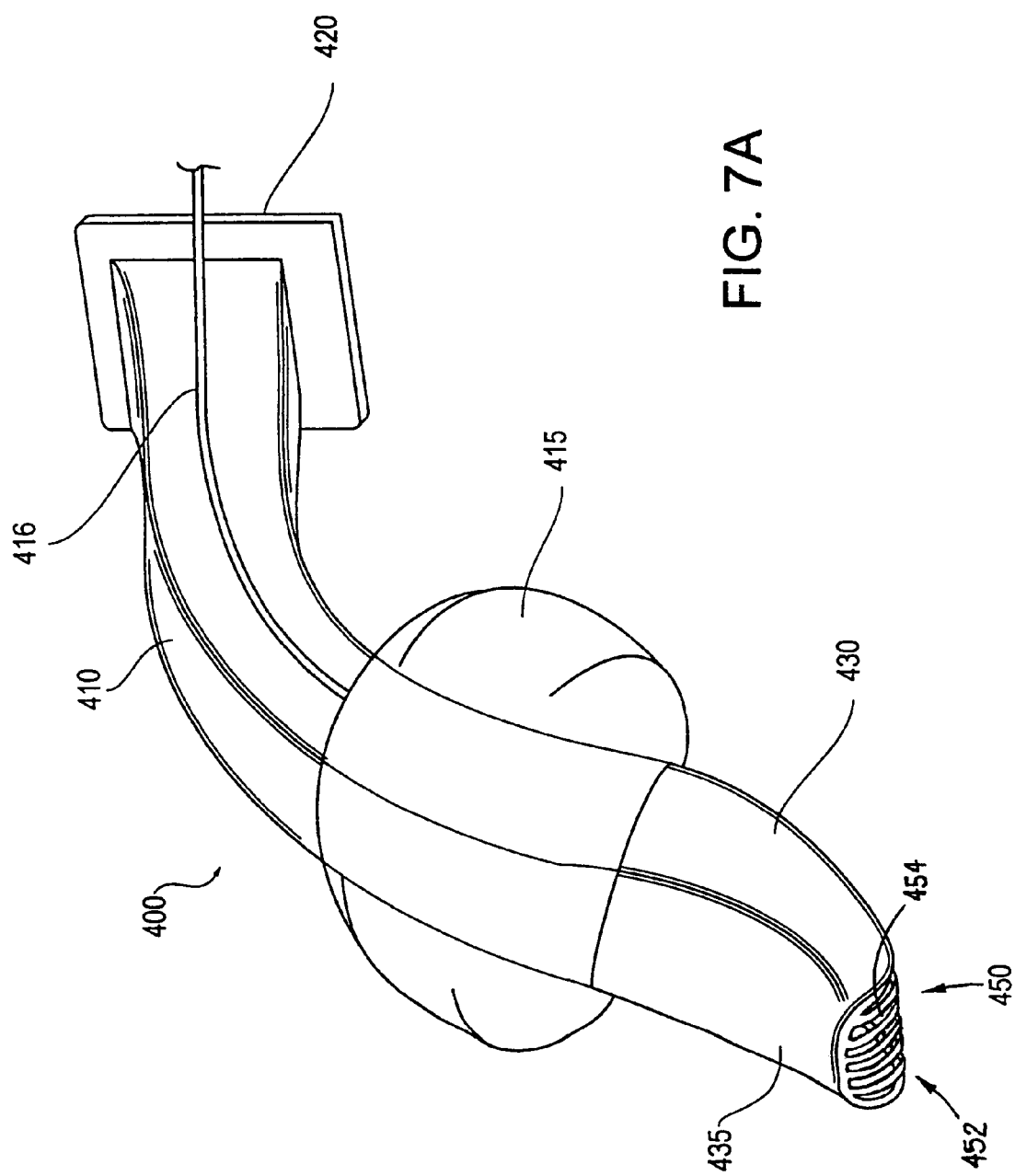

PERILARYNGEAL ORAL AIRWAY WITH TEMPERATURE SENSOR

RELATED APPLICATIONS

This application is a continuation of U.S. patent application Ser. No. 10/145,389, filed May 14, 2002 now U.S. Pat. No. 6,729,325, which is a continuation of Ser. No. 09/409,295, filed Sep. 29, 1999 now U.S. Pat. No. 6,386,199, both entitled "Perilaryngeal Oral Airway."

TECHNICAL FIELD

The present invention relates generally to a class of medical devices commonly referred to as oral airways and supraglottic airways which are inserted through a patient's mouth and into the patient's pharynx while the patient is undergoing general anesthesia or is undergoing respiratory treatment such as is carried out with cardiopulmonary resuscitation. More specifically, the present invention is directed to a perilaryngeal oral airway and perilaryngeal supraglottic airway which is capable of monitoring a patient's core body temperature.

BACKGROUND ART

Oral airways were introduced into the practice of anesthesia and cardiopulmonary resuscitation several decades ago for two basic purposes. First, they prevent the patient's biting down on and occlusion of a previously placed oral endotracheal tube. Second, and most important, oral airways help to provide a patent airway that allows positive pressure ventilation to be carried out by the practitioner. More recently, some oral airways have been developed to facilitate blind (not visually directed) placement of an endotracheal tube.

For most patients, mask ventilation is carried out successfully by insertion of an oral airway and by a variety of physical adjustments, such as extension of the patient's neck and elevation of the patient's jaw. However, in some patients, no matter what physical adjustments are made or the particular oral airway which is inserted, mask ventilation cannot be successfully achieved. Such cases are literally life-threatening as hypoxemia and death can quickly ensue if the patient's blood is deprived of oxygen due to a lack of ventilation.

When mask ventilation (even with the use of an oral airway) cannot be carried out, there are multiple mechanisms responsible. Most significantly, soft tissue structures in the hypopharynx (the area between where conventional oral airways end and the glottis opens into the trachea) collapse inwardly and obstruct airflow. This collapse occurs from both an antero-posterior direction, as well as from the sides of the hypopharynx. Unfortunately, all oral airways which have been introduced into practice to date end bluntly well above the epiglottis (the cartilaginous structure just above the glottis or laryngeal opening) and glottis and thus place patients at risk for significant airway obstruction. Another mechanism of airway obstruction which occurs while using oral airways is the patient having large lips covering the outside opening of the oral airway with subsequent inadequate airflow through the nasal passages (due to the solid posterior wall of the airway limiting passage of air into the airway at the level of the nasopharynx).

Additionally, most known oral airways are comprised of a hard plastic material throughout their length with no variation in softness between one end of the oral airway and the opposite end. As a result, the distal end (i.e., the end which first enters the mouth and passes down into the pharynx of the patient) often bruises or otherwise damages soft mucosal surfaces of the patient during insertion or once the oral airway has been seated in place.

Representative prior art airways include Baildon, U.S. Pat. No. 4,919,126, which discloses an oral airway formed of plastic which includes an air passageway extending longitudinally through the airway. The distal end has a projecting solid anterior portion which serves as an "epiglottis elevator." As such, the oral airway is blunt-shaped in configuration and ends well above the glottis. For this reason, the Baildon oral airway suffers from the problems discussed above in that it fails to provide any structure to prevent the collapse of soft tissue structures in the hypopharynx.

Berman, U.S. Pat. Nos. 4,054,135 and 4,067,331, relate to an intubating pharyngeal airway having a side access for passage of an endotracheal tube. The airway includes a blunt end on the anteriorly extending wall which is designed to fit into the vallecula (area between the epiglottis and tongue). Accordingly, the devices disclosed in both of Berman's patents are similar to the device of Baildon in that they can detrimentally allow soft tissue structures to invaginate inward and thereby occlude the passage of air.

Moses, U.S. Pat. No. 3,908,665, discloses an oro-pharyngeal airway wherein the outer diameter of the body portion progressively increases from the end closest to the mouth to the opposite end thereof so as to relieve any obstruction to the flow of air by the base of the tongue falling back on the posterior pharyngeal wall. However, the airway of Moses likewise suffers from the problems discussed in detail above in that the blunt-shaped end terminates well above the glottis, thereby allowing possible soft tissue obstruction to occur.

Augustine, U.S. Pat. No. 5,203,320, discloses a tracheal intubation guide which similarly seats above the glottis. Moreover, the device of Augustine functions as a guide for placing an endotracheal tube in a "blind" manner and is neither designed for nor could it possibly function to allow mask ventilation to be carried out.

In addition, for some patients it is important to use an airway device which provides a seal within the patient's airway (trachea, oro- or hypopharynx) in order to better allow positive pressure ventilation to be accomplished. These airways are referred to herein as superglottic airways. Traditionally, this has been achieved by using an endotracheal tube passed between a patient's vocal cords. In an effort to avoid the deleterious effects of tracheal intubation (e.g., bronchospasm, dental injury and cardiovascular stimulation), the laryngeal mask airway ("LMA") has been introduced into clinical practice. The LMA is illustrated and described in Brain, U.S. Pat. No. 4,509,514. While providing a seal with which to administer positive pressure ventilation, there are several potential problems when using an LMA. First, the device is easily malpositioned so that ventilation is not possible, for example, by virtue of the epiglottis bending back over the glottis and thereby obstructing air flow. Second, by directly covering the glottic aperture, trauma to the glottic structures (arrhytenoid cartilages, vocal cords) can occur. In addition, the cost of this product (over $200) becomes a factor when limitations to reuse occur due to physical damage of the device or accidental loss. Third, as a reusable product, the hazard of cross-contamination from one patient to another cannot be completely eliminated.

Because of the above-limitations of the LMA, a cuffed oro-pharyngeal airway has been introduced into clinical practice. Greenberg, U.S. Pat. No. 5,443,063, describes such a device as an oro-pharyngeal cuff placed over a conventional oral airway. However, this device has several significant limitations which prevent it from functioning adequately. First, the airway suffers from the problems of those previously discussed in that it ends well above the glottis, thereby allowing soft tissue obstruction to impair the flow of oxygen to the lungs. Second, with the cuff placed so far proximally in the oro-pharynx, the device tends to push itself out of the patient's mouth, thereby requiring that the device be secured in place by means of a strap placed around the patient's head. Finally, the cuff is positioned so far proximally in the patient's airway that it often allows leakage of oxygen and anesthetic gases around the cuff, thereby preventing the formation of an air-tight seal. This, of course, makes positive pressure ventilation impossible in those patients.

Several oral airways, including those described in the patents to Berman and Augustine, have been introduced into clinical practice in an effort to provide a means to accomplish blind intubation of a patient's trachea with an endotracheal tube (or to facilitate fiberoptic intubation). These devices end well above the glottic opening and thus function poorly in terms of reliably directing the end of an endotracheal tube into the glottis with blind passage. As a result, the hard distal end of the endotracheal tube may be directed against the structures which surround the glottic opening (arytenoid, cuneiform and corniculate cartilages, epiglottis, aryepiglottic folds) and cause damage to these structures or their soft tissue surfaces. Further, that damage may result in hemorrhage which obscures vision if subsequent placement of the endotracheal tube by means of a fiberoptic device is attempted. Other prior art has attempted to better direct an endotracheal tube into the glottis by having walls which surround and thus engage the arytenoid cartilages or which have projections which physically enter in between those cartilages. Representative are Patil, U.S. Pat. No. 5,720,275; Krüger, U.S. Pat. No. 4,612,927; and Williams, U.S. Pat. No. 4,338,930. However, these structures have hard advancing surfaces which can likewise cause trauma.

Recently, a version of the LMA which is meant to facilitate blind intubation with an endotracheal tube has been introduced into clinical use which attempts to surmount the problems of a misguided endotracheal tube causing trauma to perilaryngeal and glottic structures. This LMA is described in Brain, U.S. Pat. No. 5,896,858. However, in addition to sharing the above discussed problems common to all LMA's, this device relies on precise positioning so that a movable flap raises an obstructing epiglottis out of the way of an advancing endotracheal tube. Because the attached flap resides within the body of the LMA it does not physically contact the epiglottis upon insertion, but rather the advancing endotracheal tube pushes the flap up against the epiglottis to move it out of the way and thus open the glottic aperture for the endotracheal tube to enter. Perfect alignment of the recessed flap with the epiglottis is thus necessary to reliably accomplish blind placement of the endotracheal tube. However, LMA's occupy a somewhat variable and inconsistent position within the hypopharynx in relation to the precise anatomic location of the glottis (due to anatomic variability among patients as well as the distensible nature of the proximal epiglottis and hypopharynx where it resides). As a result, blind intubation with an endotracheal tube with this device can also result in tissue trauma by virtue of its advancing end being misdirected.

The importance of monitoring and maintaining core body temperature when patients undergo general anesthesia is now being more clearly recognized. Significant reductions in body temperature (which are the common and usual course following induction of general anesthesia) in patients undergoing surgery are associated with an increased incidence of cardiac morbidity, increased rates of wound infection, impaired wound healing and alterations in blood coagulation status. In addition, although rare, a patient undergoing general anesthesia may have a sudden and dramatic rise in body temperature due to an abnormal acceleration of metabolic rate in a condition termed malignant hyperthermia. This is a life-threatening syndrome which requires prompt recognition and treatment if a patient is to survive, and the rise in body temperature is one of the hallmarks used to diagnose its occurrence. Further, in order to reliably measure body temperature, a "core" temperature must be used. As such, a thermistor or thermal couple temperature probe must be in contact with a deep visceral cavity (e.g., urinary bladder, esophagus), blood, or an internal mucosal surface (e.g., hypopharynx, nasopharynx) which reflects inner body temperature as opposed to surface temperature of the patient. No supraglottic airway or oral airway which is currently in use provides measurement of core temperature by a temperature sensor incorporated into that device.

The present invention is intended to overcome one or more of the problems discussed above.

SUMMARY OF THE INVENTION

A first aspect of the present invention is an oral airway consisting of an elongate tubular member having a distal end and a proximal end. The elongate tubular member is configured to place the distal end in a supraglottic position and to prevent advancement of the distal end into a patient's larynx when operative placed within a patient. A temperature sensor is operatively associated with the elongate tubular member and is positioned on the elongate tubular member to detect a supraglottic core temperature of a patient with the distal end of the oral airway operatively placed in a supraglottic position within a patient. Preferably the temperature sensor is positioned on the elongate tubular member to contact an internal mucosal surface of the hypopharynx. The temperature sensor is preferably coupled to an external display. The elongate tubular member may include an enlarged housing at the distal end with the temperature sensor positioned on the enlarged housing. The enlarged housing may be wedge-shaped and include anterior and posterior walls forming an enlarged proximal portion tapering to a small distal portion and sidewalls extending between the anterior and posterior walls. The wedge-shaped housing is configured so that the sidewalls abut the aryepiglottic folds with the wedge-shaped housing operatively placed within they hypopharynx of a patient.

A second aspect of the present invention is a method of delivering air to a patient which includes providing an oral airway having a distal end and a proximal end with an air delivery opening near the distal end and a temperature sensor attached to the oral airway near the distal end. The oral airway is configured to prevent insertion of the distal end into a patient's larynx when operatively placed within a patient. The distal end of the oral airway is inserted into the mouth of a patient and is seated in a supraglottic operative position within the patient with the opening adjacent the glottis and the temperature sensor contacting a mucosal surface within the patient's hypopharynx.

The oral airway including a temperature sensor of the present invention allows for the accurate determination of a patient's core temperature while the patient's breathing is being assisted by the oral airway without requiring additional invasive instrumentation. The ease of use will promote the monitoring of body temperature of a patient undergoing general anesthesia and reduce the risk of the patient undergoing significant body temperature changes which can severely threaten the patient's well being.

BRIEF DESCRIPTION OF THE DRAWINGS

FIG. 4A is a perspective view showing one embodiment of the perilaryngeal oral airway according to the present invention;

FIG. 4B is a posterior view of the perilaryngeal oral airway of FIG. 4A according to the present invention;

FIG. 5A is a perspective view showing a further embodiment of the perilaryngeal oral airway according to the present invention;

FIG. 6B is a posterior view of the perilaryngeal oral airway of FIG. 6A according to the present invention;

FIG. 7 shows a cuffed embodiment of the perilaryngeal oral airway according to the present invention;

FIG. 7A shows a cuffed embodiment of the perilaryngeal oral airway according to the present invention including a grate covering the opening;

DETAILED DESCRIPTION OF THE PREFERRED EMBODIMENT

The invention will now be described with reference to the drawings; however, the position of a conventional oral airway is first briefly discussed.

Figure 1:
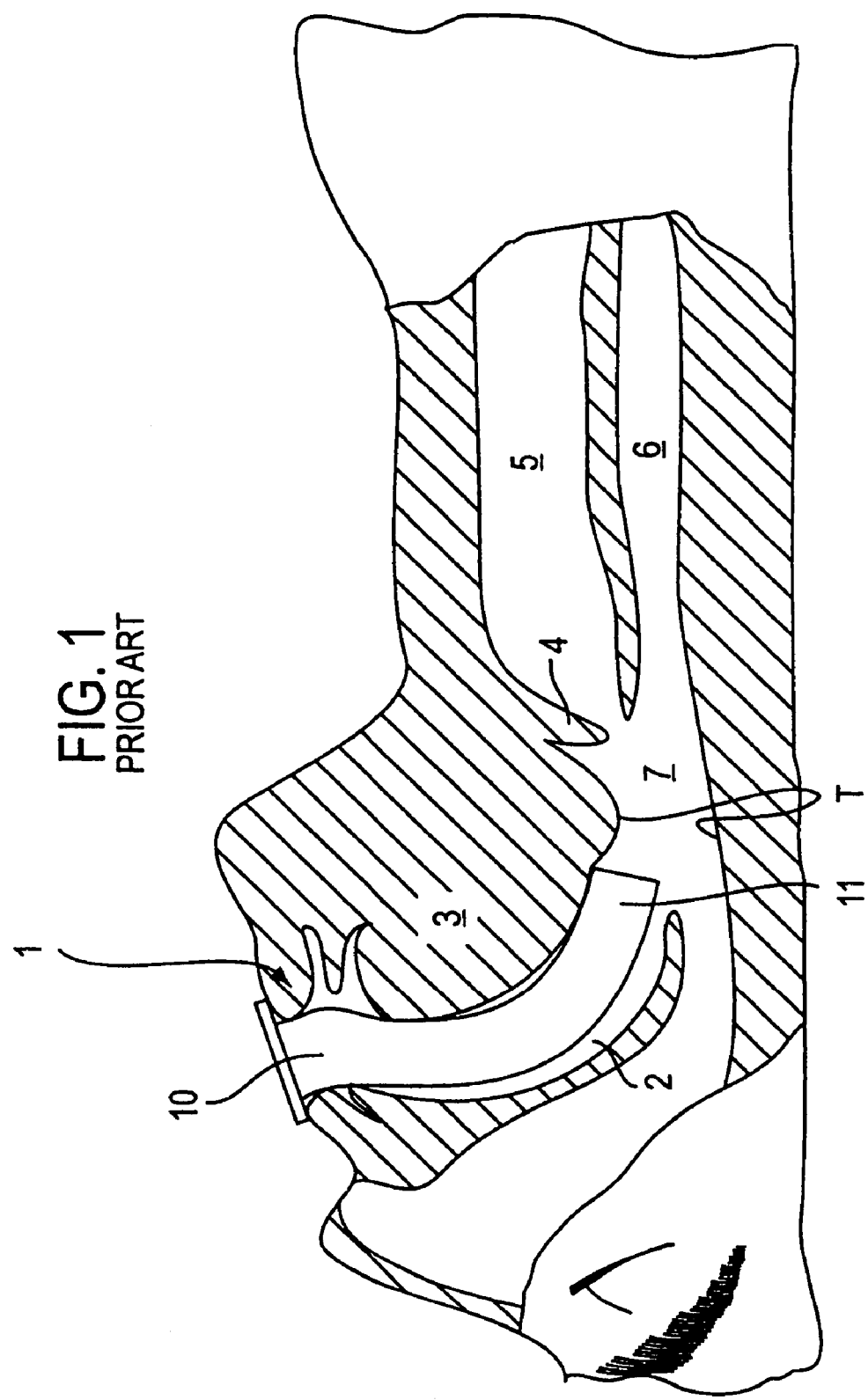
FIG. 1 is a cross-sectional side view illustrating the use of a conventional oral airway inserted into a patient.
Figure 2:
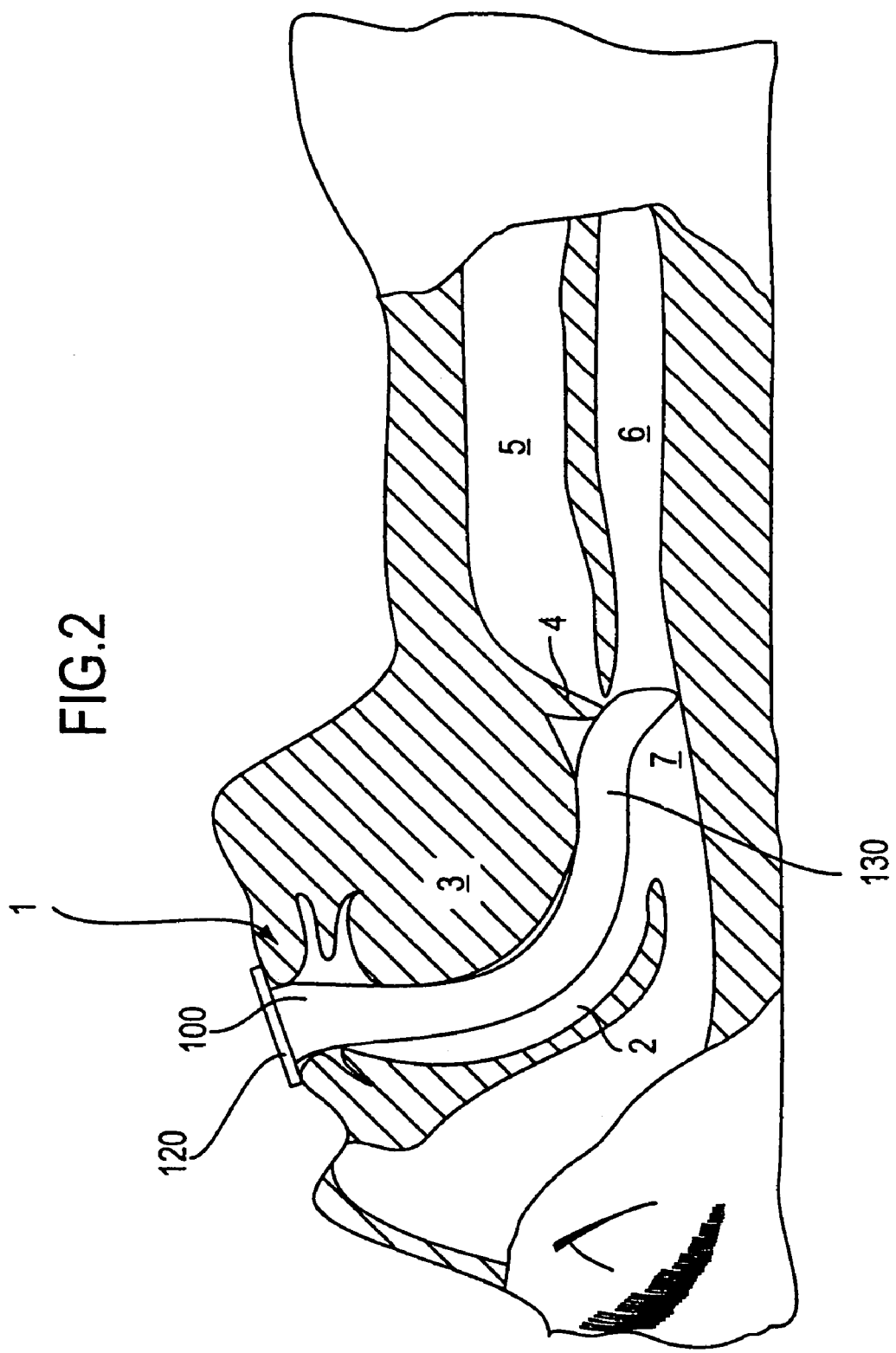
FIG. 2 is a cross-sectional side view illustrating the use of the perilaryngeal oral airway in accordance with one embodiment of the present invention.

FIG. 1 shows a simplified anatomical illustration of a patient's head, including the oral airway defined by the mouth 1, the oral cavity 2, the tongue 3, and the epiglottis 4, the trachea 5, the esophagus 6 and the hypopharynx 7. A conventional oral airway 10 is positioned within the patient's oral airway, with the distal end 11 ending well above the glottis so that no structure is provided to prevent the collapse of soft tissue structures T in the hypopharynx.

FIGS. 2, 3, 4A and 4B relate to one embodiment of the perilaryngeal oral airway according to the present invention. Note that in FIG. 2, like elements are denoted with like reference numerals with reference to the patient's oral airway.

Referring to FIGS. 4A and 4B, the perilaryngeal oral airway 100 includes a curved hollow, tubular longitudinally extending body member 110. The curvature of the body member preferably, but not necessarily, is between 100° and 140°. The body member 110 includes a flanged proximal end portion 120 for location at the mouth of the patient (see FIG. 2). The body member 110 further includes a distal end portion 130 for insertion into the mouth and pharynx of the patient. In the first embodiment, the distal end portion 130 of the body member 110 is divided so as to form a pair of elongated extension walls 140 and 141 which are operative to seat deep in the patient's hypopharynx and surround the patient's epiglottis and glottis (see FIGS. 2 and 3), thereby to hold the patient's soft tissue away from the patient's air channel opening.

A U-shaped or V-shaped opening or notch 150 is formed in the distal end portion 130 of the body member 110 so as to form the two elongated extension walls 140 and 141 and into which the epiglottis and glottis are positioned. The elongated extension walls 140 and 141 at the distal end portion preferably, but not necessarily, expand outward laterally to allow for sufficient space in which to accommodate the epiglottis and glottis within the U-shaped or V-shaped opening 150. The extreme distal ends 160 and 161 of the elongated extension walls 140 and 141, respectively, may be angled inwardly slightly, thereby providing a smooth contour. The purpose of the inwardly angled extreme distal ends is to allow the ends to be safely inserted past the tonsillar pillars at the back of the patient's mouth. By forming the inwardly-shaped surface, the slightly narrower most distal end can push up against very large tonsils and move them laterally to the sides as the perilaryngeal oral airway is inserted.

The elongated lateral extension walls 140 and 141 are preferably, but not necessarily, formed to be relatively flexible and soft so that there is at least some "give" as the perilaryngeal oral airway is inserted into the patient. The particular firmness of the walls must strike a balance between the need to hold the hypopharyngeal and perilaryngeal structures away from the glottis, the need to move the soft tonsillar and oro-pharyngeal structures to the side as the oral airway is inserted, and the desire for the oral airway to be able to bend inwardly when inserted through the back of the patient's mouth. Likewise, the body member 110 of the perilaryngeal oral airway 100 is preferably, but not necessarily, of sufficient softness and pliability to bend during insertion and to accommodate different angles once it is successfully inserted into the patient, since a given patient's head and neck may be slightly flexed or extended to provide optimal positioning for mask ventilation. The most proximal end portion 120 of the oral airway is much harder than the distal end portion 130 in order to prevent occlusion by the patient biting down thereon.

Figure 5B:
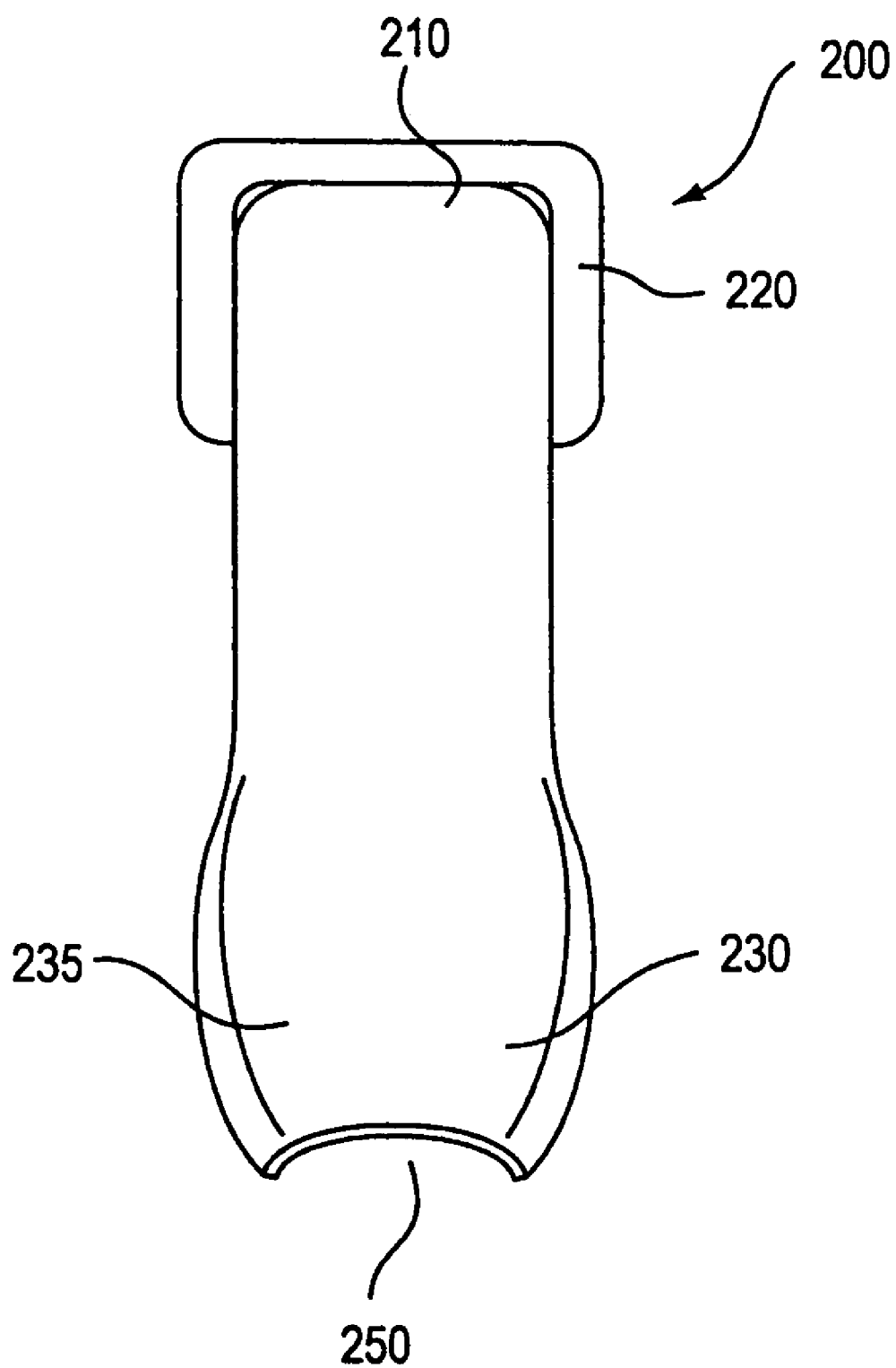
FIG. 5B is a posterior view of the perilaryngeal oral airway of FIG. 5A according to the present invention.

FIGS. 5A and 5B show a further embodiment of the perilaryngeal oral airway according to the present invention wherein the distal end portion 230 is modified in comparison to the oral airway of the previous embodiment. Note that like elements are denoted with like reference numerals, but preceded by the reference number "2". In particular, in this embodiment, the distal end portion 230 has a "filled-in" distal posterior wall 235 in order to better hold tissue away from the larynx. The anterior wall includes a notched portion 250 as in the previous embodiment. The body member 210 of the oral airway preferably, but not necessarily, is of sufficient softness and pliability to bend during insertion and to accommodate different angles once successfully inserted into the patient.

Figure 6A:
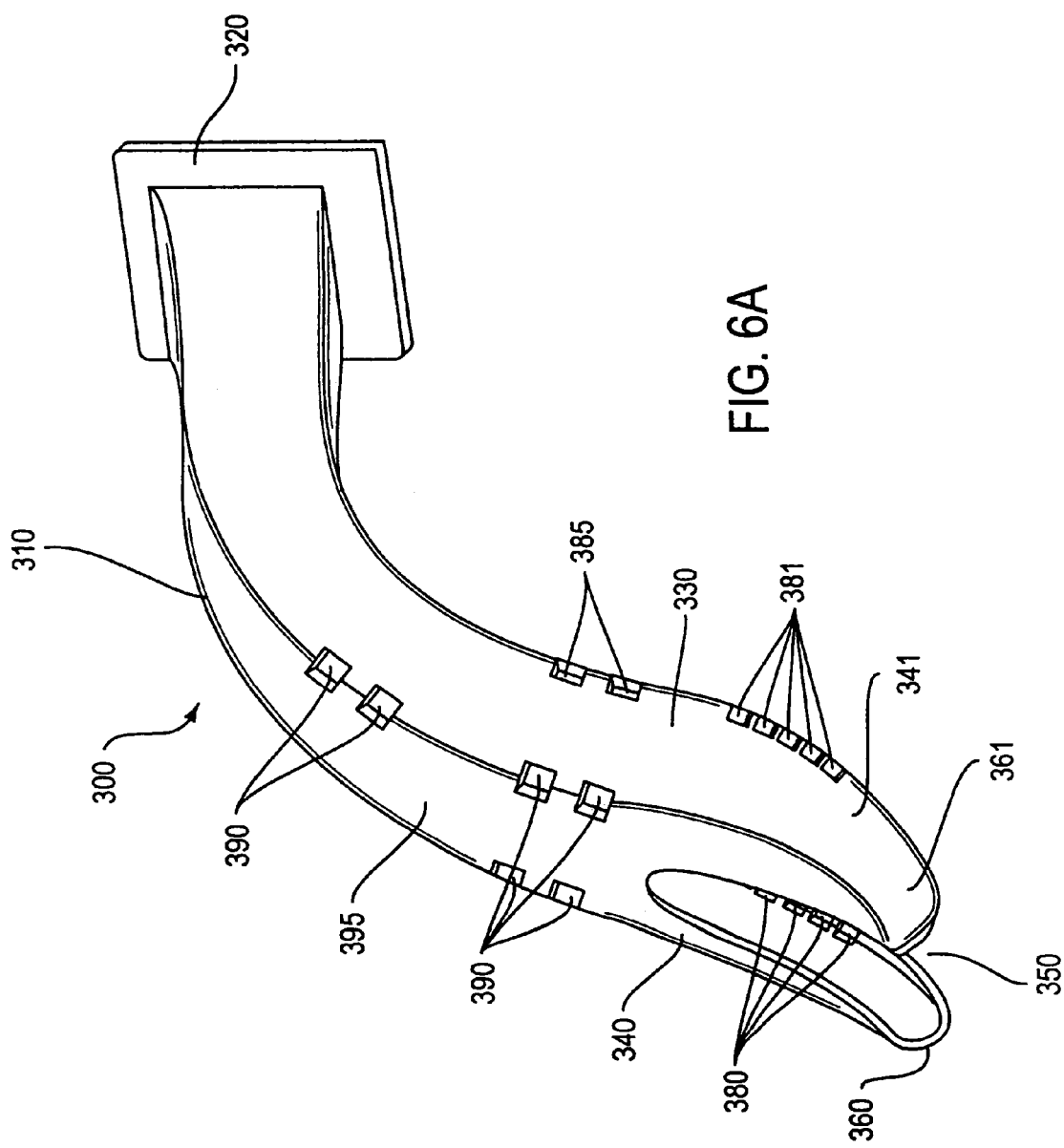
FIG. 6A illustrates the use of holes or fenestrations in one of the embodiments of the perilaryngeal oral airway according to the present invention.

FIGS. 6A and 6B illustrate a still further embodiment of the perilaryngeal oral airway according to the present invention. Again, like elements are denoted with like reference numerals, but preceded by the number "3". In particular, holes or fenestrations 385 may be formed through the distal anterior wall of the body member 310 of the oral airway in order to provide ventilation should the distal end portion 330 be positioned directly over the glottic opening of the patient, as might occur if the practitioner has selected too large of an oral airway for a particular patient, or where the patient has an abnormally high (rostrally) placed glottic opening.

Moreover, holes 380 and 381 may be formed through the anterior surface of the elongated extension walls 340 and 341, respectively, and which function to allow ventilation should the oral airway be situated at an abnormal angle such that one of the elongated extension walls covers the glottis.

Still further, additional air holes or fenestrations 390 may be formed through the posterior wall 395 of the body member 310 of the oral airway at the region of curvature which is adapted to be positioned at the back of the oropharynx and which allows passage of air through the nasal passages of the patient and into the oral airway per se.

Of course, while the holes and fenestrations are shown in connection with the first embodiment of the present invention which includes the elongated extension walls 340 and 341, the holes or fenestrations may likewise be used with the second embodiment which includes the filled-in distal posterior wall. Of course, the holes can be dispensed with entirely in both the first and second embodiments if desired.

Figure 3:
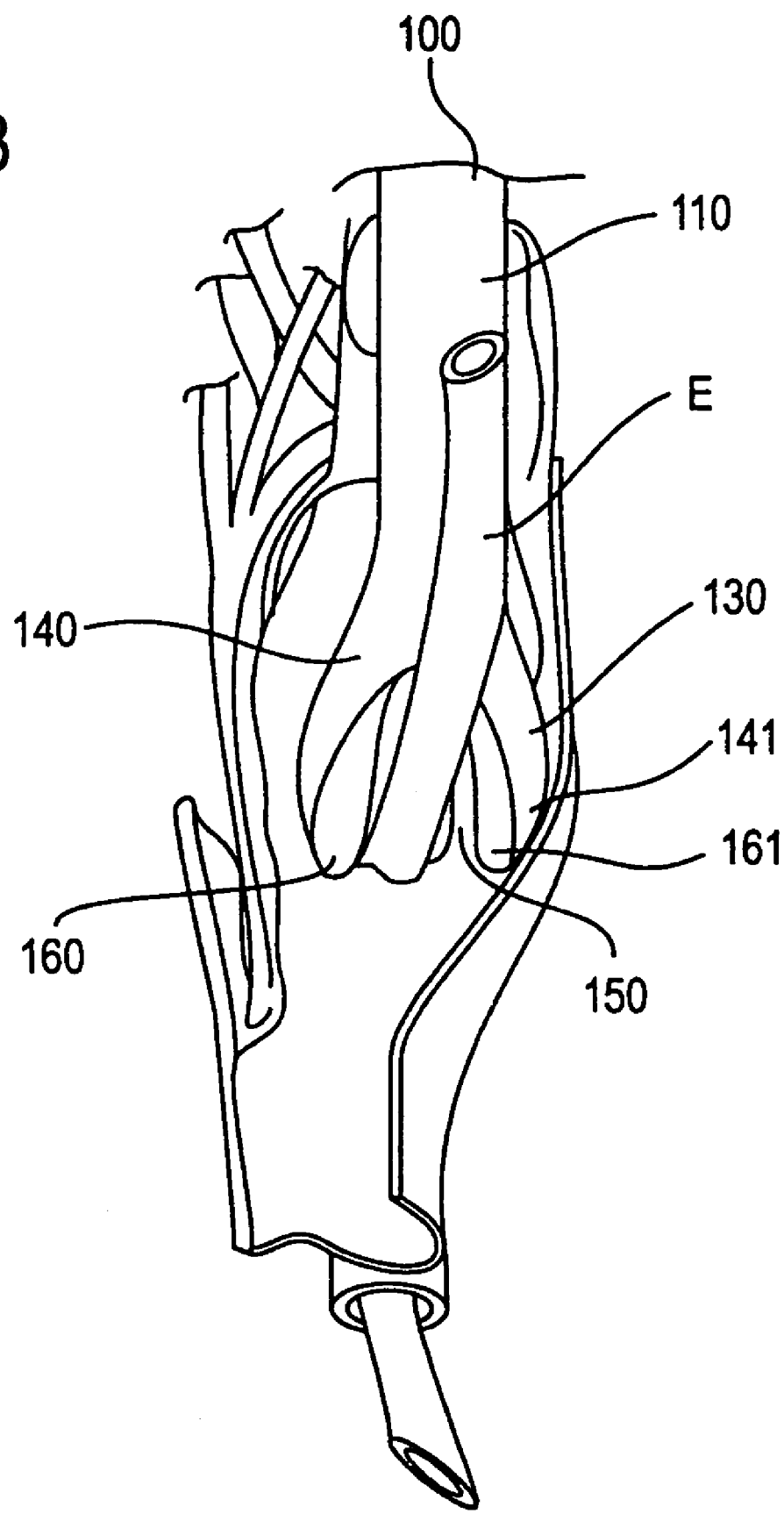
FIG. 3 is a schematic view of the pharynx of a patient wherein the posterior wall has been removed and the interior is viewed from behind, with the distal end portion of one embodiment of the perilaryngeal oral airway according to the present invention being shown seated in position and with an endotracheal tube E in situ.

Referring to FIG. 3, the anterior and posterior U- or V-shaped grooves or notches receive an endotracheal tube E. When a patient is presently intubated with the endotracheal tube E, the body member 110 can receive a proximal end of the endotracheal tube and be axially inserted into the mouth and pharynx of a patient over the endotracheal tube and seated as illustrated in FIG. 3. When intubation is no longer required, the endotracheal tube E can be removed and body member 110 is properly seated to retain the surrounding soft tissue and maintain an oral airway as may be necessary.

FIG. 7 shows yet a further embodiment which includes an inflatable cuff 415 placed just above the distally positioned anterior notch 450. FIG. 7A further includes a plurality of bars 452 forming a grate over the leading opening 454. Again, like elements are denoted with like reference numerals, but preceded with the number "4". The grate or bars 452 cause the epiglottis to slide into abutment with an anterior portion of the end portion 430 of the body member 410. As discussed below with reference to FIG. 11, the bars are rigid enough to support the epiglottis but flexible enough to allow an endotracheal tube to be inserted therebetween. The cuff 415 is designed to be inflatable using a pilot tube 416 which includes a self-sealing proximal valve (not shown).

Upon inflation, the more distally positioned inflated cuff of the present invention is located within the hypopharynx and thereby allows the perilaryngeal oral airway of the present invention to be held in place without external means and avoids the airway leakage which can occur at the base of the tonsillar pillars and soft palate when using the conventional cuffed oro-pharyngeal airway.

Figure 8:
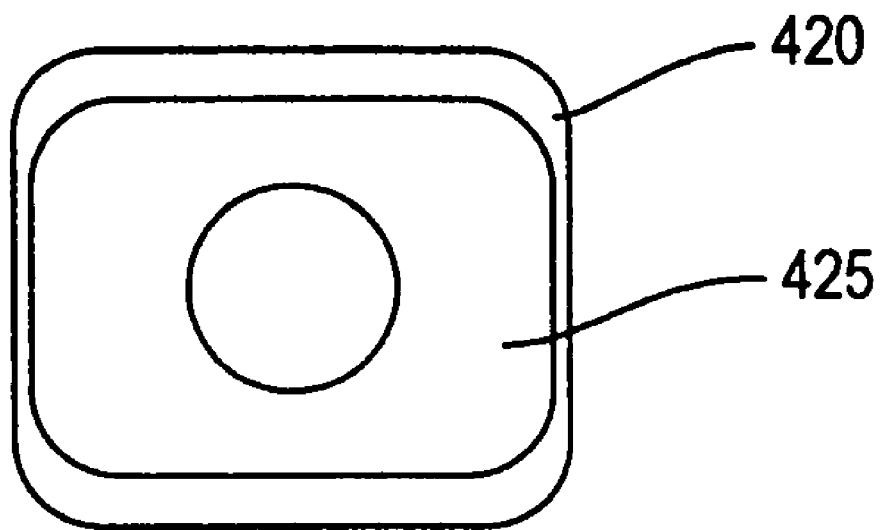
FIG. 8 shows a proximal end of the perilaryngeal oral airway of FIG. 7.

As shown in FIG. 8, in order to allow the cuffed airway 400 to be attached to an anesthesia circuit or other airway circuit, an adapter 425 is inserted into the flanged proximal end portion 420 of the oral airway. In the embodiment of FIGS. 7 and 8, the adapter 425 is placed inside the flanged proximal end portion 420 of the oral airway 400 and held in by means of friction. However, many other mechanisms (e.g., Luer-lock, notched, snap, etc.) may be utilized to retain the adapter 425 in the proximal end 420 of the oral airway. Alternatively, the adapter may be made so as to fit over the end of the perilaryngeal oral airway and still accomplish the desired purpose. Of course, the proximal end piece for permitting attachment to an anesthesia circuit or other airway circuit may be molded into the oral airway itself.

With respect to all of the above-discussed embodiments, the actual lumen or hollow portion of the perilaryngeal oral airway of the present invention may be dome-shaped (convex) at the posterior wall of the body member at least through the portion which is operative to be positioned within the patient's mouth in order to better approximate the anatomy of the oral passageway.

Moreover, as an alternative, the oral airway may terminate in the hypopharynx (below the base of the tongue) but still end above the epiglottis, so that it would function to hold soft tissues away from the air passageway. A further embodiment of this particular alternative might have both the anterior and posterior notch absent since it could terminate just above the epiglottis.

FIGS. 9, 10, 11, 14 and 15 relate to another embodiment of the perilaryngeal oral airway according to the present invention. Note that in FIGS. 14 and 15 as well as FIG. 16, like elements are denoted with like reference numerals with reference to the patient's oral airway.

Figure 9:
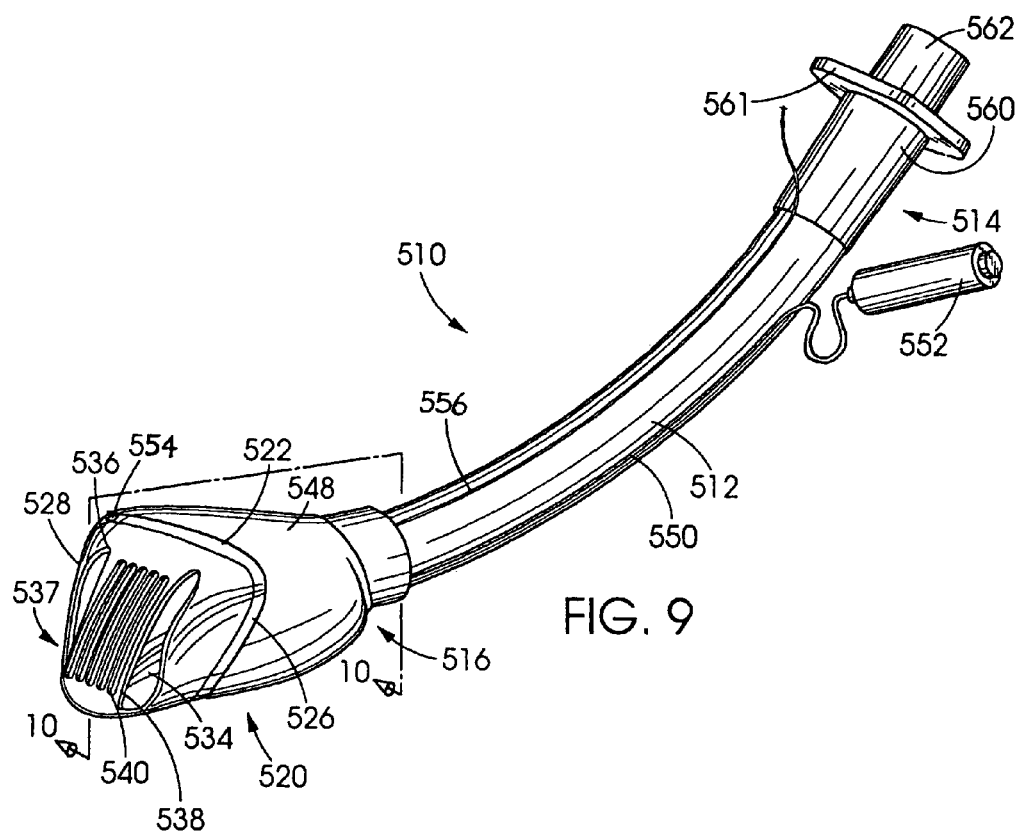
FIG. 9 is a perspective view of a grated embodiment of the perilaryngeal oral airway according to the present invention.
Figure 14:
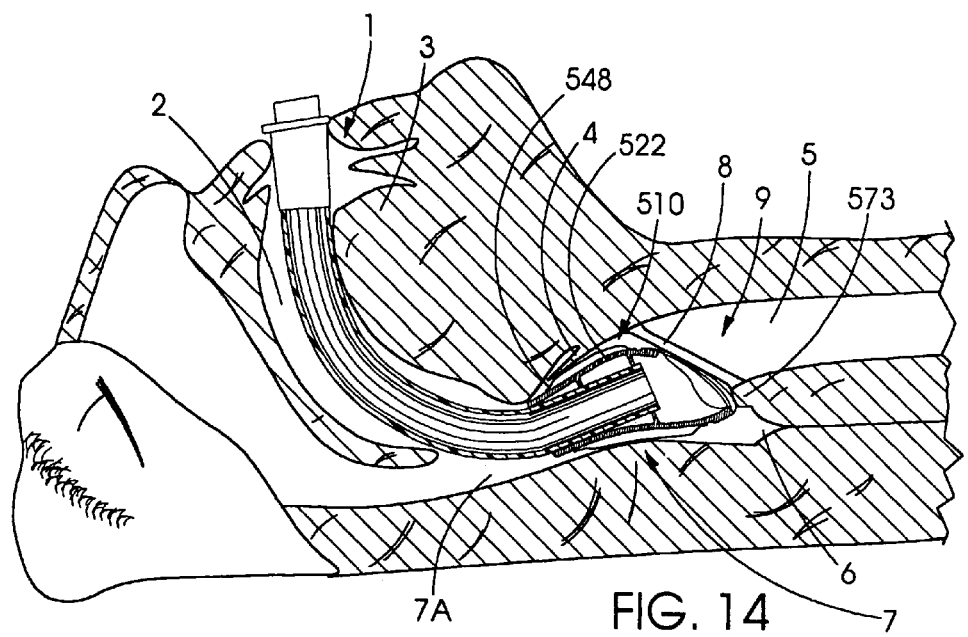
FIG. 14 is a cross-sectional side view illustrating the grated perilaryngeal oral airway according to the present invention nested in the hypopharynx of a patient.
Figure 15:
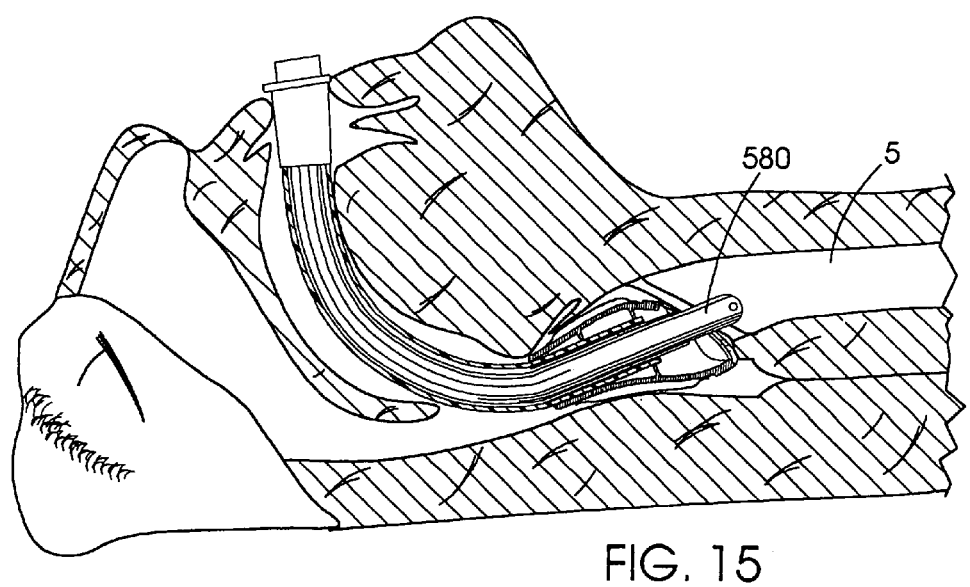
FIG. 15 is a cross-sectional side view identical to FIG. 14 only with an endotracheal tube being guided into the trachea of a patient.
Figure 16:
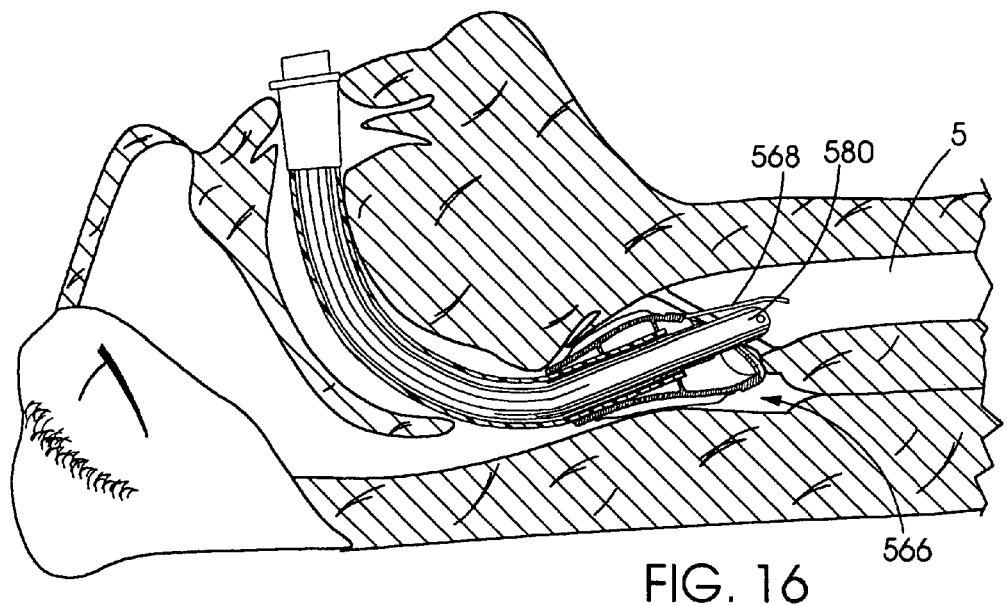
FIG. 16 is a cross-sectional side view identical to FIG. 14 only with the hinged grate housing embodiment and an endotracheal tube extending into the trachea of a patient.

The embodiment of the perilaryngeal oral airway illustrated in FIG. 9 will be referred to herein as the grated oral airway or the grated PLA 510. The grated PLA 510 consists of an elongate tubular member 512 having a proximal end 514 and a distal end 516. Attached to the distal end 516 of the elongate tubular member 512 is a wedge-shaped housing 520. The wedge-shaped housing 520 has an anterior wall 522, a posterior wall 524 and sidewalls 526, 528 extending therebetween. The anterior wall abuts an anterior portion of a patient's hypopharynx and the posterior position abuts a posterior portion of patient's hypopharynx when seated as illustrated in FIGS. 14–16. As best viewed in FIG. 17, the anterior and posterior walls 522, 524 form an enlarged proximal portion 530 of the wedge-shaped housing which tapers to a smaller distal portion 532. The housing is sized to seat deep in the patient's hypopharynx. The leading opening 534 separates the anterior and posterior walls from the distal end of the housing and extends from the distal end of the posterior wall 524 to a recess in the anterior wall at 536. In this manner, the opening 534 is inclined between the distal end of the posterior wall and the recess 536 in the anterior wall. A grate 537 covers the leading opening, with the grate being inclined between the posterior and the anterior walls. In the embodiment illustrated in FIG. 9, the grate comprises a plurality of parallel bars 538 separated by a plurality of gaps 540 extending between the posterior wall 524 and anterior wall 522.

Figure 10:
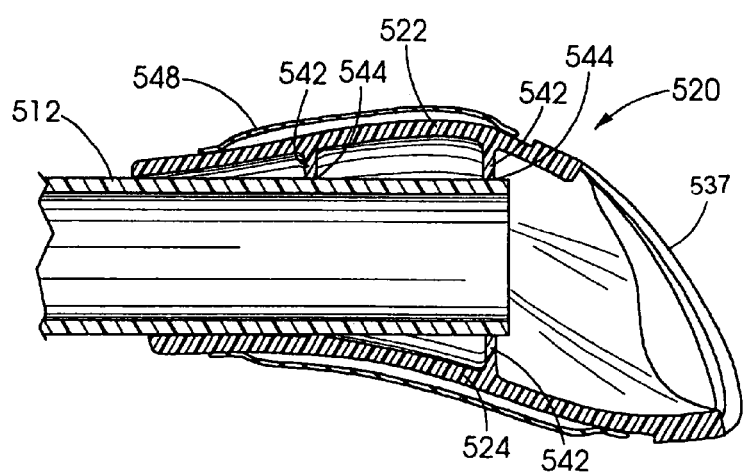
FIG. 10 is a cross-section view of the distal end of the grated perilaryngeal oral airway taken along line 10—10 of FIG. 9.
Figure 17:
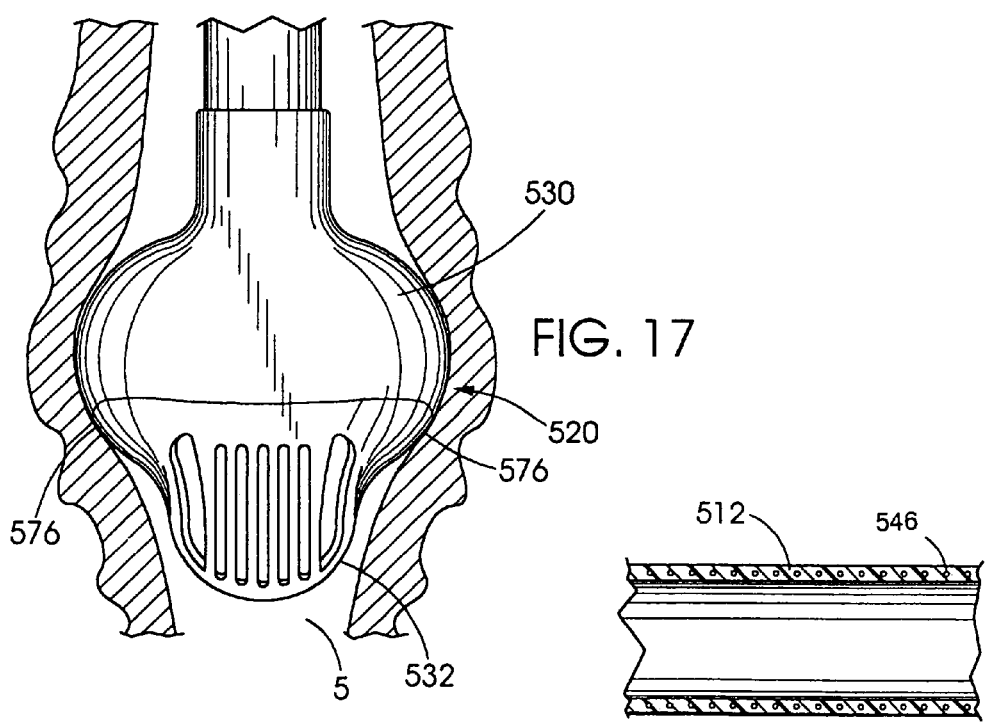
FIG. 17 is a schematic cross-sectional front view illustrating the grated perilaryngeal oral nested in the hypopharynx of a patient.
Figure 18:
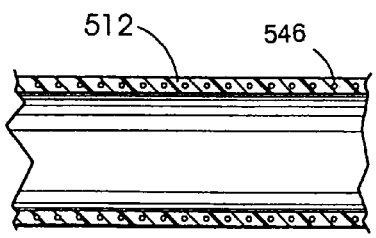
FIG. 18 is a cross-sectional side view of a reinforced elongate tubular member in accordance with the present invention.

The grated PLA 510 including the elongate tubular member and the wedge-shaped housing 520 may be integrally formed in a single manufacturing step from polyvinyl chloride or another suitable thermoplastic. In the preferred embodiment, however, the wedge-shaped housing is manufactured in two pieces divided substantially along the line 10—10 of FIG. 9. Referring to FIG. 10, internal supports 542 are integrally formed with each position of the housing and define circular orifices 544 that receive the distal end of the elongate tubular member 512 therein. The elongate tubular member is heat staked, sonic welded or otherwise permanently bonded to the housing. In the embodiments illustrated in FIGS. 9–18, the tubular member is shown as having a round cross-section, although the tubular member may have a number of cross-sectional configurations including oval, square or rectangular, provided the elongate tubular member includes a hollow lumen. The tubular member can be slightly contoured as illustrated in FIG. 9 or straight. The tubular member is preferably made of a material such as polyvinyl chloride or other thermoplastic that is substantially axially rigid yet radially flexible so that when inserted within the mouth, oral cavity and pharynx of a patient, it may follow the anatomical contours. It is also preferably sufficiently flexible so that a surgeon operating on the oral cavity or pharynx with the grated PLA in place can axially deflect the tubular member out of the operating theater. The tubular member further is radially robust to not kink during insertion or manipulation. As illustrated in FIG. 18, the tubular member may include wire reinforcing 546 wound into its wall.

The wedge-shaped housing 520 further includes an inflatable cuff 548 that surrounds the wedge-shaped housing 520 radially about the enlarged proximal portion 530 of the wedge-shaped housing 520. As illustrated in FIGS. 9 and 10, the inflatable cuff 548 extends both proximal and distal of the largest effective diameter of the enlarged proximal portion 530. Alternatively, the inflatable cuff 548 may be located on the tubular member proximate the proximal end of the wedge-shaped housing 520 as illustrated with the embodiment of FIG. 7. A pilot tube 550 extends from the cuff along the elongate tubular member so as to be able to extend out of the mouth of a patient and terminates at its proximal end with a self-sealing proximal valve 552. With the cuff in its uninflated state, it closely envelops the exterior surface of the wedge-shaped housing 520. When in its inflated state, as illustrated in FIG. 14, the cuff extends radially sufficiently to fully occlude the surrounding pharynx or hypopharynx so as to enable a practitioner to apply positive pressure ventilation.

The grated PLA 510 preferably further includes a temperature sensor 554 shown mounted to the anterior wall 522 of the wedge-shaped housing 520 in FIG. 9. Alternatively, the temperature sensor 554 can be located on one of the sidewalls 526, 528, the posterior wall 524 or even on the inflatable cuff 548. The temperature sensor 554 is connected to a lead 556 which extends along the length of the elongate tubular member 512 coupling to an external display or monitor (not shown).

At the proximal end 514 of the elongate tubular member is a bite block 560 having a flanged end 561. The bite block 560 can be integrally formed from a thickened side of the tubular member 512 or be a more rigid plastic or metal collar that is slid over the proximal end 514 and held in place by friction or an adhesive. In addition, an adaptor 562 may be placed inside the flanged end 561 of the bite block 560 and may be permanently affixed or releasably held in place by means of friction or other mechanisms such as a Luer-lock, notch, snap or the like. It may also be integrally formed with the bite block 560 in a single manufacturing step.

Figure 12:
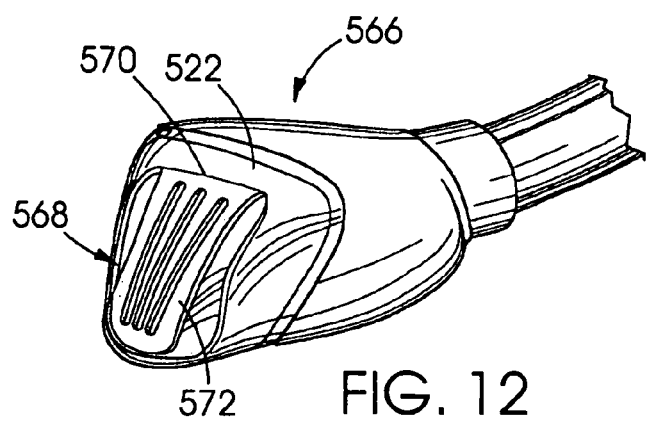
FIG. 12 is a perspective view of a hinged grate embodiment of the housing of FIG. 9.
Figure 13:
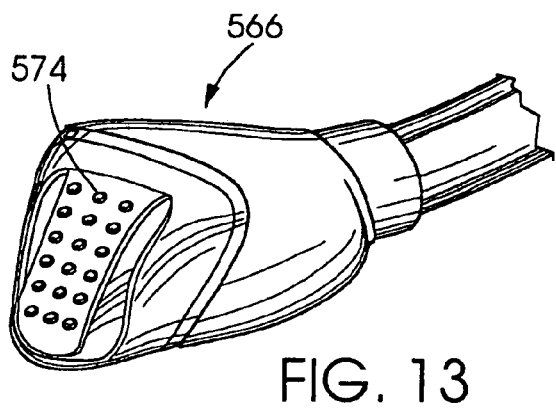
FIG. 13 is a perspective view of another embodiment of the hinged grate housing of FIG. 12.

FIG. 12 illustrates an alternate embodiment of the wedge-shaped housing referred to herein as the hinged grated PLA 566. This embodiment is identical to that described above with regard to FIGS. 9 and 10 except the grate 568 is attached only to the anterior wall 522 by a hinge 570. By virtue of the hinge, the grate 568 can be pivoted open as illustrated in FIG. 16. As illustrated in FIG. 12, the hinged grate 572 has a plurality of vertically extending bars 572. Alternatively, as illustrated in FIG. 13, the hinged grate can be a solid flap with a plurality of holes 574 therein. Although not shown, the grate could also be a solid flap as opposed to a perforated grate. The hinge 570 can be a separate structure joining the grate 568 onto the anterior wall 522 or a living hinge, under which circumstances the anterior wall 522 and the grate 568 are integrally formed in a single manufacturing step.

FIG. 14 is a simplified anatomical cross-section of a patient's head and neck with the various anatomic features indicated by the same references numbers used with FIG. 1. Additional relevant anatomic features include the vocal chords 8 and the glottis or larynx generally indicated at 9. The various cartilage and muscular tissue comprising the glottis or larynx, with the exception of the vocal chords 8, has been eliminated for the sake of clarity.

In use, the wedge-shaped housing 520 of the grated PLA 510 is axially inserted in the mouth 1 of a patient and the elongated tubular member 512 bends to conform to the anatomical contours of the oral cavity 2, pharynx 7A, hypopharynx 7 so that the wedge-shaped housing 520 rests within the hypopharynx as illustrated in FIG. 14. The housing is made of a material that is flexible and soft to provide some give as it is inserted into a patient so as to prevent damage to the soft tissue of the pharynx and hypopharynx. However, the housing is sufficiently rigid to prevent its collapse by this same tissue as it is inserted into and seated within a patient. Likewise, the grate must be of sufficient rigidity to separate these tissues and to allow the epiglottis to ride up it.

The grate 537 is inclined so that as the grate encounters the epiglottis 4, the epiglottis rides up the grate and comes to rest abutting the anterior wall 522 of the wedge-shaped housing 520. More particularly, as viewed in FIG. 14, the epiglottis abuts the inflatable cuff 548. The axial insertion of the wedge-shaped housing is intended to be arrested by the sidewalls of the enlarged proximal portion 530 coming into abutment with the aryepiglottic folds 576 as illustrated in FIG. 17. As illustrated in FIGS. 14–16, with the grated PLA 510 or the hinged grated PLA 566 properly seated, the epiglottis abuts the anterior wall of the wedge-shaped housing and the leading opening 534 is adjacent to the vocal chords 8 and the glottis or larynx 9. In addition, the distal end of the housing may abut the tissue 578 dividing the trachea 5 and esophagus 6. In this manner, all the soft tissue surrounding the hypopharynx and larynx is held back from the leading opening 534 and an unobstructed airway is provided to the trachea 5 for unassisted patient breathing.

The PLA illustrated in FIG. 14 can also be used to provide respiratory assist or anesthesia of a patient. In this application, once the PLA is seated as illustrated in FIG. 14, the inflatable cuff 548 is inflated so as to form a seal in the patient's hypopharynx 7. In fact, the cuff is shown so inflated in FIG. 14. A principle advantage of placing the cuff at the enlarged portion of the housing is less air is required to inflate it to occlude the pharynx. Also, by having the cuff on the housing as it inflates it further serves to spread tissue and keep the airway formed by the PLA open. A respiratory circuit or anesthesia circuit (not shown), as conditions require, is attached to the distal end of the elongate tubular member by the adaptor 14.

Figure 11:
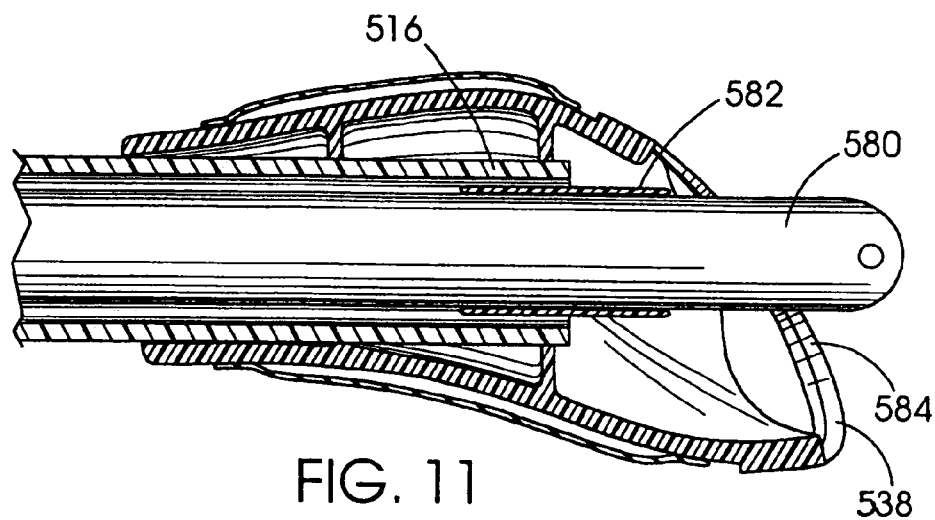
FIG. 11 is a cross-sectional view identical to FIG. 10 only with an endotracheal tube axially inserted in the elongate tubular member.

The grated PLA 510 is also intended to allow blind intubation of a patient with an endotracheal tube 580 having an inflatable cuff 582 or to insert some other instrument into the trachea of a patient. Referring to FIG. 11, the bars 538 of the grate 537 are flexible enough so that an endotracheal tube can be inserted into a gap 540 between adjacent bars and deform the bars as shown at 584 in FIG. 11 to extend axially therebetween. Referring to FIG. 15, the distal end 516 of the tubular member 512 is received with in the housing so that as the endotracheal tube 574 is axially advanced through the bars 538 of the grate 537, it is directed anteriorly into the trachea 5 of a patient. In this manner, a patient may be reliably blindly intubated with a high degree of confidence that the endotracheal tube will be properly seated in the trachea.

FIG. 16 illustrates the hinged grate embodiment 566 of the wedge-shaped housing 520 being used to intubate a patient with a endotracheal tube 580. In this embodiment, as the endotracheal tube 580 is axially advanced into contact with the hinged grate 568 it pivots the hinged grate open anteriorly so that the endotracheal tube 580 can extend into the patient's trachea 5 as illustrated.

What is claimed is:

1. An oral airway comprising:
    an elongate tubular member having a distal end and a proximal end;
    means operatively associated with the distal end of the elongate tubular member for preventing advancement of the distal end into a patient's larynx and for placing the distal end in the supraglottic position with the oral airway operatively placed within a patient; and
    a temperature sensor operatively associated with the elongate tubular member, the temperature sensor being positioned relative to the elongate tubular member to detect a supraglottic core temperature of a patient with the distal end of the oral airway operatively placed in a supraglottic position within the patient.

2. The oral airway of claim 1 wherein the temperature sensor is operatively associated with the elongate tubular member to contact an internal mucosal surface of the hypopharynx with the distal end of the oral airway operatively placed a supraglottic position within the hypopharynx of the patient.

3. The oral airway of claim 1 wherein the temperature sensor is coupled to an external display.

4. The oral airway of claim 1 wherein the means for preventing advancement of the distal end into a patient's larynx comprises an enlarged housing at the distal end of the elongate tubular member, the temperature sensor being positioned on the enlarged housing.

5. The oral airway of claim 4 wherein the enlarged housing is wedge-shaped.

6. The oral airway of claim 5 wherein the wedge-shaped housing comprises anterior and posterior walls forming an enlarged proximal portion tapering to a smaller distal portion and side walls extending between the anterior and posterior walls, the wedge-shaped housing being configured so that the side walls abut the aryepiglottic folds with wedge-shaped housing operatively placed within the hypopharynx of a patient.

7. The oral airway of claim 6 wherein the temperature sensor is attached to the wedge-shaped housing, the temperature sensor being adapted so that with the wedge-shaped housing operatively placed within the hypopharynx of a patient, the temperature sensor contacts a mucosal surface within the patient's hypopharynx.

8. The oral airway of claim 1 further comprising an inflatable cuff on the tubular member near the distal end, the temperature sensor being attached to the inflatable cuff so that with the distal end in the operative position within the hypopharynx and the cuff in an inflated state, the temperature sensor contacts an internal mucosal surface of the patient.

9. A method of delivering air to a patient comprising:
    providing an oral airway having a distal end and a proximal end with an air delivery opening near the distal end and a temperature sensor operatively associated with the oral airway near the distal end, the oral airway further having operatively associated with the distal end means for preventing insertion of the distal end into a patient's larynx when the oral airway is operatively placed within a patient;
    inserting the distal end into the mouth of the patient; and
    seating the distal end in a supraglottic operative position within the patient with the opening adjacent the glottis and the temperature sensor contacting a mucosal surface within the patient's hypopharynx.

10. The method of claim 9 wherein the means for preventing insertion of the distal end into a patient's larynx comprises an enlarged wedge-shaped housing, the wedge-shaped housing having anterior and posterior walls forming an enlarged proximal portion tapering to a smaller distal portion, the method further comprising seating the distal end in a supraglottic operative position with a leading surface of the enlarged proximal portion abutting the patient's aryepiglottic folds.

11. The method of claim 9 further comprising monitoring the patient's core temperature using the temperature sensor.

12. The method of claim 9 wherein the temperature sensor is spaced from the air delivery opening a distance sufficient to prevent air delivered from the air delivery opening from degrading the accuracy of a core temperature sensed by the temperature sensor.

13. An oral airway comprising:
    an elongate tubular member having a leading distal end and a proximal end, the leading distal end leading the tubular member as it is inserted into the mouth and pharynx of a patient, there being an opening at the leading distal end and the leading distal end having operatively associated therewith means for arresting insertion of the leading distal end in a supraglottic position within a patient's hypopharynx when operatively placed within a patient; and
    a temperature sensor operatively associated with the elongate tubular member, the temperature sensor being positioned relative to the elongate tubular member to detect a supraglottic core temperature of a patient with the distal end of the oral airway in a supraglottic operative position within the hypopharynx of a patient.

14. The oral airway of claim 13 further comprising a grate covering the opening, the grate being configured so that as a patient's epiglottis is engaged by the grate during insertion of the distal end into the hypopharynx, the epiglottis slides up the grate and into abutment with an anterior portion of the tubular member.

15. The oral airway of claim 13 wherein the temperature sensor is positioned relative to the elongate tubular member to contact an internal mucosal surface of the hypopharynx with the distal end of the oral airway in a supraglottic operative position within the hypopharynx of a patient.

16. The oral airway of claim 13 further comprising an inflatable cuff on the tubular member near the distal end, the temperature sensor being attached to the inflatable cuff so that with the distal end in the operative position within the hypopharynx and the cuff in an inflated state, the temperature sensor contacts an internal mucosal surface of the patient.

* * * * *